United States Patent [19]

Simpson et al.

[11] Patent Number: 4,771,774
[45] Date of Patent: Sep. 20, 1988

[54] MOTOR DRIVE UNIT

[75] Inventors: John B. Simpson, Woodside; Hanson S. Gifford, III, Palo Alto; Kenneth A. Stenstrom, Manteca, all of Calif.

[73] Assignee: Devices for Vascular Intervention, Inc., Redwood City, Calif.

[21] Appl. No.: 31,168

[22] Filed: Mar. 26, 1987

Related U.S. Application Data

[63] Continuation of Ser. No. 834,743, Feb. 28, 1986, abandoned.

[51] Int. Cl.⁴ .............................................. A61B 17/32
[52] U.S. Cl. .................................................. 128/305
[58] Field of Search ............. 128/305, 305.1, 751–755, 128/304, 303 R; 604/22

[56] References Cited

U.S. PATENT DOCUMENTS

| | | | |
|---|---|---|---|
| 4,002,169 | 1/1977 | Cupler | 128/305 X |
| 4,320,761 | 3/1982 | Haddad | 128/305 |
| 4,445,509 | 5/1984 | Auth | 128/752 X |

*Primary Examiner*—Michael H. Thaler
*Attorney, Agent, or Firm*—Flehr, Hohbach, Test, Albritton & Herbert

[57] ABSTRACT

Motor drive unit for use with an atherectomy device having a flexible drive cable and a finger operated member for advancing and retracting the drive cable. The drive unit comprises a motor and a power supply mounted in a case of a size which fits comfortably in a human hand, with a power switch positioned for operation by a finger of the hand holding the case. When the motor is connected to the drive cable, the finger operated member can be operated by a finger of the hand holding the case to advance and retract the cable and the cutter connected thereto.

9 Claims, 1 Drawing Sheet

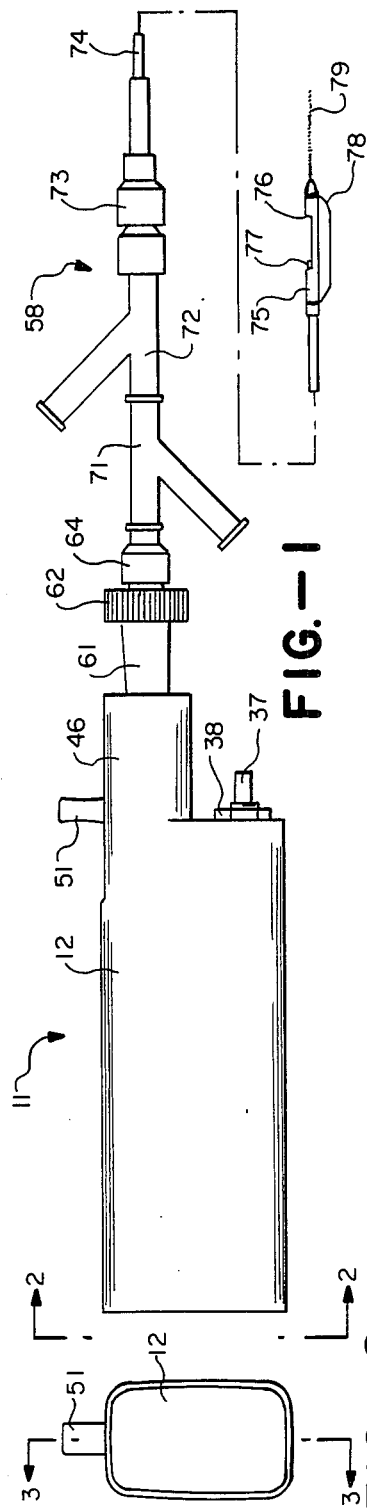
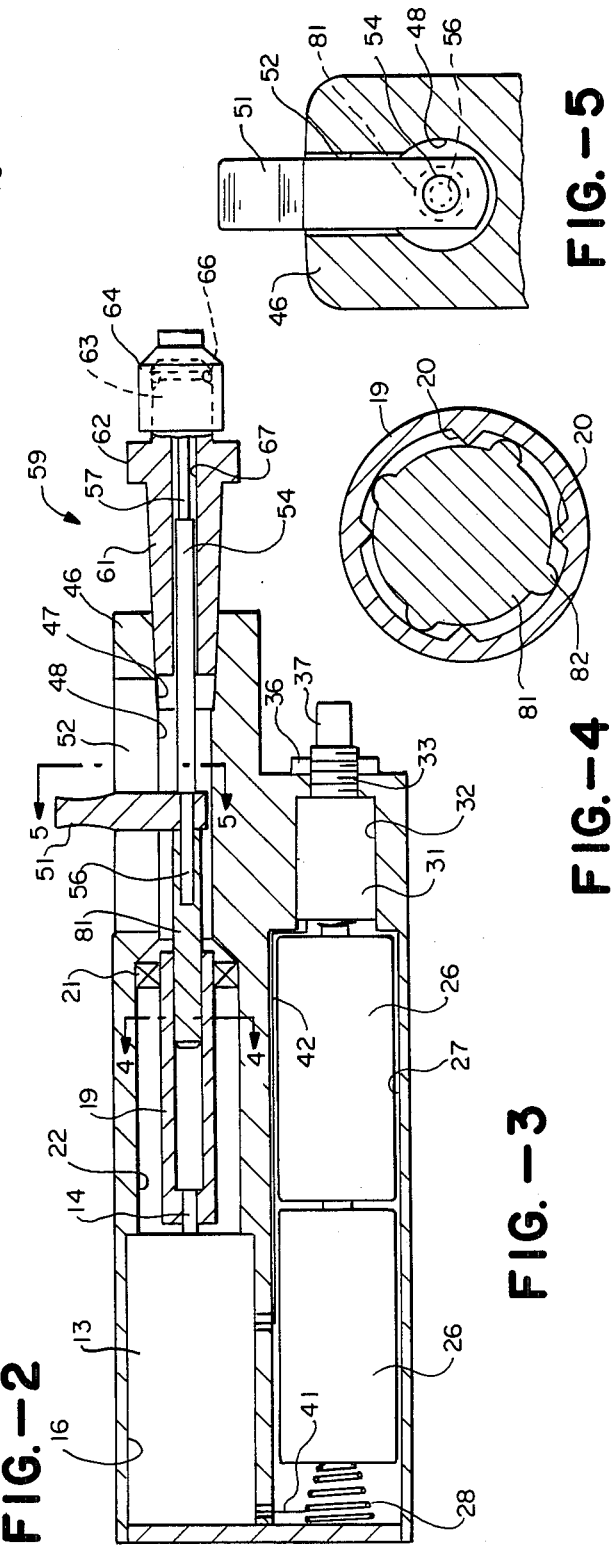

MOTOR DRIVE UNIT

This is a continuation of application Ser. No. 834,743, filed Feb. 28, 1986, now abandoned.

This invention relates to a motor drive unit and more particularly, to a motor drive unit for use with an atherectomy device.

In co-pending application, Ser. No. 732,691 filed on May 10, 1985, there is disclosed a motor drive unit for an atherectomy device. However, it has been found that the motor device disclosed therein has certain disadvantages. For example, it is difficult to ascertain the relative motion of the cutter with respect to the catheter. In addition, it was necessary to hold the motor drive unit in one hand and the catheter in the other hand to create relative motion between the two. There is therefore a need for a new and improved motor drive unit for use with atherectomy devices.

In general, it is an object of the invention to provide a motor drive unit which is particularly useful in connection with atherectomy devices.

Another object of the invention is to provide a motor drive unit of the above character which provides an indication of relative motion between the cutter and the catheter of the atherectomy device.

Another object of the invention is to provide a motor drive unit of the above character which can be readily separated from the drive cable.

Another object of the invention is to provide a motor drive unit of the above character which has an inexpensive construction so that it can be disposed of after use.

Additional objects and features of the invention will appear from the following description in which the preferred embodiments are set forth in conjunction with the accompanying drawings.

FIG. 1 is a side elevational view of a motor drive unit incorporating the present invention attached to an atherectomy device.

FIG. 2 is an end elevational view looking along the line 2—2 of FIG. 1.

FIG. 3 is a cross-sectional view of the motor drive unit shown in FIG. 1 taken along the line 3—3 of FIG. 2.

FIG. 4 is a cross-sectional view taken along the line 4—4 of FIG. 3.

FIG. 5 is a cross-sectional view taken along the line 5—5 of FIG. 3.

In general, the motor drive unit of the present invention is for use with an atherectomy device having a flexible drive cable with cooperative engagement means carried by the proximal extremity of the drive cable and having a finger operated member carried by the flexible drive cable for advancing and retracting the drive cable. A case is provided which has a size so that it can comfortably fit in a human hand. A motor is mounted in the case. A power supply is also mounted in the case for operation of the motor. Switch means is carried by the case and is accessible from the exterior of the case so that it can be operated by a finger of the hand holding the case. Cooperative engagement means is carried by the case and is coupled to the motor to be driven by the motor and is adapted to make a connection to the cooperative engagement means of the atherectomy device. Means is carried by the case for receiving the finger operated member when the cooperative engagement means of the atherectomy device and the cooperative engagement means carried by the case are joined together so that the finger operated member can be operated by a finger of the hand holding the case.

More in particular, the motor drive unit 11 of the present invention is comprised of a case or housing 12. The case 12 is relatively elongate and is substantially oval in cross-section as shown in FIG. 2. The case or housing 12 can be formed of any suitable material. For example, it can be formed of an injection molded plastic so as to give the case an attractive appearance.

A gear head motor 13 is provided in the case. The gear head motor 13 can be of a suitable type such as Micromo model 1624 with a 16/2 gear head. The gear head motor 13 is provided with an output shaft 14 which can be driven at a suitable speed, as for example, from 1500 to 3000 rpm and preferably at a speed of approximately 2500 rpm. The gear head motor 13 is mounted in a compartment 16 provided in the case 12. A hollow shaft extension 19 is provided which has circumferentially spaced apart triangularly-shaped splines 20 therein on the interior surface thereof that serve as the cooperative connection means as hereinafter described. The outer extremity of the shaft extension 19 is rotatably mounted in a bearing 21 which is carried by the case 12. The bearing 21 as well as the hollow shaft extension 19 are disposed within a compartment 22 provided in the case 12.

A power supply is provided in the case and takes the form of a pair of batteries 26 which are mounted in a compartment 27 in the case immediately below the motor compartment 16. The batteries 26 are arranged in series and have one end of one battery engaging a coil spring 28 and having the other end of the other battery engaging a contact 29 carried by a switch 31. The switch 31 is mounted in a compartment 32 within the case and is provided with a threaded extension 32 which extends through a hole 34 provided in the case 12. The extension 32 is held in place by a nut 36 threaded onto the extension. A finger operated push button 37 is carried by the extension 33 and is adapted to be engaged by a finger of the same hand which holds the case 12. Conducting wires 41 and 42 are provided for establishing an electrical connection between the batteries 26 and the gear head motor 13 under the control of the switch 31.

The case 12 is provided with a forwardly extending extension 46 which is provided with a tapered bore 47 facing forwardly therefrom. The bore 47 is in communication with a passage 48 provided in the extension and which opens into the hollow shaft extension 19.

A finger operated slide or flipper member 51 is removably mounted in the extension 46 of the case 12 and extends through a slot 52 provided in the case 12. The lower extremity of the finger member 51 is disposed within the passage 48 and has a hole 54 (see FIG. 5) therein through which a shaft 56 rotatably extends. The shaft 56 is carried by the proximal extremity of the flexible drive cable 57 and is fastened thereto by suitable means such as crimping. The shaft 56 is provided with an enlarged portion 56a. The flexible drive cable 57 with the flipper member 51 carried thereby forms a part of an atherectomy device of the type described in co-pending application Ser. No. 732,691 filed on May 10, 1985. As described therein, the atherectomy device 58 is comprised of a fitting 59 which is provided with a proximal tapered portion which is adapted to be seated within the tapered bore 47 of the extension 46 of the motor drive unit 11. The fitting 59 is provided with a knurled flange or knob 62 and with a threaded extension 63. The threaded extension 63 is adapted to be threaded into the proximal end of a fitting 64 and to form a fluid-tight seal with respect to an O-ring 66 carried by the fitting 64. The fitting 59 is provided with a bore 67 through which the shaft 56 extends.

The fitting 64 forms a part of the atherectomy device and as shown forms a part of an adapter 71. The adapter 71 is mounted in another adapter 72. The adapter 72 is mounted in a fitting 73 carried by the proximal extremity of a flexible guide tubing 74. A housing 75 having a cutout 76 is carried by the distal extremity of the flexible guide tubing 74. A cutter 77 is rotatably and slidably mounted in the housing 75 and is secured to the flexible drive cable 57. An inflatable balloon 78 is carried on the exterior of the housing on the side opposite where the cutout 77 appears. A flexible guide wire 79 is secured to the distal extremity of the housing 75.

A drive spline 81 is secured to the proximal extremity of the shaft 56 and is provided with circumferentially spaced apart elongate splines 82 which are semicircular in cross section. The drive spline 81 is sized so that it can readily enter the splined hollow drive shaft 19 by pushing the drive spline 81 into the shaft 19. The clearance between the spline 20 and 82 is such that an insertion can be made with ease. The finger member 51 is held in place by the drive spline 81 and is positioned so it can enter the slot 52 as the drive spline 81 is inserted into the splined hollow drive shaft 19. The drive spline 81 and the splined hollow drive shaft extension 19 serve as coopertive connection means.

Operation and use of the motor drive unit 11 for operating an atherectomy device 58 may now be briefly described as follows. Let it be assumed that the atherectomy device has been inserted into a vessel in the vascular system of a patient in the proper position and that the balloon 78 has been inflated and it is desired to operate the cutting device carried by the housing 75. To accomplish this, the proximal extremity of the atherectomy device 58 in the form of the drive spline 81 is inserted by introducing it into the passage 48 of the extension 46 of the case 12 and into the splined hollow shaft extension 19 carried by the case 12 at the same time the finger member 51 is positioned so it enters the slot 52 in the case 12. The drive spline 81 is held in place by urging the tapered portion 61 of the fitting 59 into the tapered bore 47 of the extension 46 of the case 12.

As soon as this has been accomplished, the case 12 can be grasped by the hand of the physician and the index finger of the hand can be utilized to operate the push button to supply energy to the drive motor 13 to cause operation of the same which in turn will cause rotation of the flexible drive cable 57 and the cutter 77 driven thereby at a relatively high speed as, for example, 2500 rpm. The thumb of the same hand of the physician can then be utilized for engaging the finger operated slide or finger member 51 to advance the finger member 51 in the slot 52. Movement of the finger member 51 moves the shaft 56 and the flexible drive cable 57 attached thereto and the cutter 77 attached to the drive cable 57. The slot 52 is of such a length so that the cutter carried by the housing 75 can be advanced throughout the entire length of the cutout 77 provided by the housing. After the finger member 51 has been moved as far forward as possible, it can be retracted by placing the thumb of the hand on the other side of the finger member 51 and pulling the same backwards in the slot 52.

Alternatively, the finger member 51 can be retained in its extreme forward position and the atherectomy device can be removed from the patient. The material which has been cut from the atheroma may be cleaned out of the housing and thereafter, the atherectomy device can be again inserted into the patient for a further cutting operation if that is still desired. In removing the atherectomy device, it is readily apparent that if desired, the motor drive unit 41 can be readily disconnected from the atherectomy device merely by separating the friction type fitting 61 from the housing and removing the drive spline 81 from the splined hollow shaft extension 19.

From the foregoing description it can be seen that the motor drive unit can be readily turned on and off by operating the switch 37. As explained previously, the switch 37 can be operated by the index finger of the hand which is holding the motor drive unit. Similarly, the thumb of the same hand holding the motor drive unit can be utilized for operating the finger member 51 for advancing and retracting the cutter in the housing of the atherectomy device. The position of the finger member 51 relative to the case 12 gives an excellent indication of the position of the cutter 77 in the cutout 76. The case is constructed in such a manner that the batteries and the motor drive can be inserted from the rear of the case. As can be seen, the device is constructed in such a manner that it can be manufactured relatively inexpensively so that if desired, the motor drive unit can be manufactured as a disposable device. If desired, the device can be reutilized by mere sterilization of the same. The construction of the motor drive unit is such that the atherectomy device can be readily connected to and disconnected from the motor drive unit.

What is claimed is:

1. In a motor drive unit for use with an atherectomy device of the type having a flexible elongate catheter with a proximal extremity, a fitting connected to the proximal extremity of the catheter, a flexible drive cable extending through the fitting and the catheter, cooperative emgagement means carried by the proximal extremity of the flexible drive cable and finger operated means carried by the flexible drive cable for moving the flexible drive cable in the fitting and in the catheter in a direction longitudinally of the axis of rotation of the flexible drive cable, the motor drive unit comprising a case sized and formed so that it can comfortably fit into a human hand, the case having a forwardly facing surface and an extension protruding distally beyond the forwardly facing surface, said extension being formed with a slot for slidably receiving the finger operated means carried by the flexible drive cable permitting the finger operated means to extend outwardly from the case so that it can be engaged by the thumb of the human hand carrying the case, a motor mounted in the case, a battery mounted in the case, switch means mounted in the forwardly facing surface of the case to extend outwardly from the case so that it can be engaged by the index finger of the hand carrying the case for energizing the motor from the battery, the case having means carried by the extension for receiving the fitting so that the fitting and the catheter connected thereto can be removably connected to the case, and cooperative engagement means driven by the motor and carried by the case and adapted to make connection with the cooperative engagement means carried by the flexible drive cable of the atherectomy device, said cooperative engagement means carried by the case permitting relative sliding movement between the cooperative engagement means carried by the case and the cooperative engagement means carried by the flexible drive cable and permitting movement of the flexible drive cable longitudinally of the axis of rotation of the flexible drive cable by the finger operated means whereby the flexible drive cable can be advanced and retracted independent of the movement of the case in a direction longitudinal of the axis of rotation of the flexible drive cable while it is being rotated.

2. A motor drive unit as in claim 1 wherein the cooperative connection means carried by the case and the cooperative connection means carried by the flexible drive cable are in the form of splined connections.

3. A motor drive unit as in claim 1 wherein said finger operated means is adapted to be slidably mounted in the case for movement longitudinally of the case.

4. A motor drive unit as in claim 3 wherein the finger operated means has a member which extends out of the case in a direction which is substantially perpendicular to the axis of rotation of the cooperative engagement means.

5. In the combination of a motor drive unit and an atherectomy device, the atherectomy device comprising a flexible elongate catheter having a proximal extremity, a fitting carried by the proximal extremity, a flexible drive cable having a proximal extremity and extending through the fitting and the catheter and being rotatably and axially movable therein, cooperative engagement means carried by the proximal extremity of the drive cable and having finger operated means carried by the flexible drive cable for moving the flexible drive cable in a direction longitudinal to the axis of rotation of the flexible drive cable, the motor drive unit comprising a case having a front surface and having a passage having an exterior opening at its distal extremity for slidably receiving said cooperative engagement means carried by the flexible drive means and a slot in communication with said passage and having an exterior opening at its distal extremity for slidably receiving said finger operated means, the casing being sized so that it can be comfortably fitted into a human hand, a motor mounted in the case, a battery operated power supply mounted in the case, switch means mounted in said front surface of the case and accessible from the exterior of the case by a finger of the hand carrying the case for energizing the motor from the power supply and cooperative engagement means driven by the motor and carried by the case and coupled to the cooperative engagement means carried by the proximal extremity of the flexible drive cable and permitting movement of the flexible drive cable longitudinally of the axis of rotation of the flexible drive cable, said case being formed so that at least a portion of said finger operated means extends through said slot and is accessible to a finger of the hand carrying the case so that it can be operated by the same hand that carries the case and operates the switch means whereby the flexible drive means can be advanced and retracted independent of movement of the case in a direction longitudinal of the axis of rotation of the flexible drive cable while the flexible drive cable is being rotated.

6. A combination as in claim 5 wherein said cooperative engagement means carried by the case and the cooperative engagement means carried by the proximal extremity of the cable are provided with splines.

7. A combination as in claim 5 wherein said switch means includes a push button underlying the finger operated means which is accessible to a finger of the hand carrying the motor drive unit so that it can be operated by the same hand that is carrying the motor drive unit.

8. A combination as in claim 7 wherein said casing has an extension protruding distally from the front surface, said slot and said passage extending through said extension.

9. In the combination of a motor drive unit and an atherectomy device, the atherectomy device comprising a catheter having proximal and distal extremities, a flexible drive cable disposed within the catheter for movement both rotationally and axially therein, cutting means carried by the distal extremity of the drive cable, finger operated means carried by the proximal extremity of the drive cable for moving the drive cable axially relative to the catheter, the motor drive unit comprising a case sized to fit comfortably into a human hand and having a front surface and an extension protruding forwardly from the front surface, the extension having a bore extending therethrough and a slot extending radially of the bore and opening into the bore, a motor mounted in the case, a power supply mounted in the case and a pushbutton switch carried by the front surface of the case and underlying the extension and being accessible from the exterior of the case and adapted to be engaged by a finger of the hand carrying the case for energizing the motor from the power supply, the proximal extremity of the drive cable being disposed in the bore in the extension and being coupled to said motor with said finger operated means being disposed in said slot whereby the flexible drive cable can be advanced and retracted independent of movement of the case in a direction longitudinal of the axis of rotation of the flexible drive cable while it is being rotated by the motor by moving the finger operated means longitudinally within the slot with a finger on the same hand that carries the case and actuates the switch.

* * * * *